US008151633B2

(12) United States Patent
Jamison et al.

(10) Patent No.: US 8,151,633 B2
(45) Date of Patent: Apr. 10, 2012

(54) METHODS AND SYSTEMS FOR CHARACTERIZING LCM PARTICLE PLUGGING AND RHEOLOGY IN REAL TIME

(75) Inventors: Dale Jamison, Humble, TX (US); Robert Murphy, Houston, TX (US); J. G. Savins, Dallas, TX (US)

(73) Assignee: Halliburton Energy Services Inc., Duncan, OK (US)

( * ) Notice: Subject to any disclaimer, the term of this patent is extended or adjusted under 35 U.S.C. 154(b) by 651 days.

(21) Appl. No.: 12/328,836

(22) Filed: Dec. 5, 2008

(65) Prior Publication Data

US 2010/0139387 A1    Jun. 10, 2010

(51) Int. Cl.
    *G01N 11/04* (2006.01)
(52) U.S. Cl. .................. 73/54.14; 73/54.13; 73/54.28; 73/54.36; 73/54.37; 73/54.39
(58) Field of Classification Search .............. 73/54.14, 73/54.13, 54.39
    See application file for complete search history.

(56) References Cited

U.S. PATENT DOCUMENTS

| 3,016,734 | A * | 1/1962 | Kabelitz et al. ............. 73/54.09 |
| 5,086,646 | A | 2/1992 | Jamison et al. ................... 73/65 |
| 6,330,826 | B1 | 12/2001 | Meeten ..................... 73/152.62 |
| 6,584,833 | B1 | 7/2003 | Jamison et al. ............. 73/61.63 |
| 6,638,049 | B1 * | 10/2003 | Moss et al. ................... 425/145 |
| 6,755,079 | B1 | 6/2004 | Proett et al. ............... 73/152.18 |
| 6,931,916 | B2 | 8/2005 | Zamora et al. .............. 73/61.63 |
| 2003/0130596 | A1 | 7/2003 | Von Der Goltz ............. 600/573 |
| 2005/0269085 | A1 | 12/2005 | Cowan .......................... 166/276 |
| 2006/0197255 | A1 | 9/2006 | Tsujimoto ..................... 264/216 |
| 2010/0018294 | A1 * | 1/2010 | Tonmukayakul et al. ... 73/54.28 |

OTHER PUBLICATIONS

International Search Report in PCT/GB2009/002807 Feb. 12, 2009.
Loeppke G E et al., "A Full-Scale Facility for Evaluating Lost Circulation Materials and Techniques", Transactions, Geothermal Resources Council, vol. 7, pp. 449-454, Oct. 1983.
Aadnoy B S et al., "Desing of Well Barriers to Combat Circulation Losses ", SPE Drilling and Completion, Society of Petroleum Engineers, vol. 23, No. 3, Sep. 2008.
International Search Report for International Application No. PCT/GB2009/002807 mailed on Mar. 18, 2010.
Saasen. A., Dawei Liu, Marken C. D., "Prediction of Barite Sag Potential of Drilling Fluids from Rheological Measurements," Drilling Conference, Amsterdam, PAYS-BAS (Feb. 28, 1995) pp. 663-671 (10 ref.).

(Continued)

*Primary Examiner* — Hezron E Williams
*Assistant Examiner* — Paul West
(74) *Attorney, Agent, or Firm* — John W. Wustenberg; Baker Botts LLP

(57) ABSTRACT

Methods and systems for characterizing drilling fluids laden with LCM (Lost Circulation Material) and other solid materials are disclosed. A test cell for analyzing a fluid is provided with a first conical inner portion and an axial positioning device positioned along an axis of the test cell. A first conical plug is coupled to the axial positioning device and is movable in and out of the first conical inner portion along the axis of the test cell. A fluid inlet is positioned at a first location on the test cell and a fluid outlet at a second location.

6 Claims, 10 Drawing Sheets

OTHER PUBLICATIONS

William Dye, Terry Hemphill, William Gusler and Gregory Mullen, "Correlation of Ultra-Low Shear Rate Viscosity and Dynamic Barite Sag in Inver-Emulsion Drilling Fluids," SPE annual technical conference, Houston, TX, ETATS-UNIS (Mar. 10, 1999), pp. 543-553 (17 ref.).

Ahmadi Tehrani, Mario Zamora and David Power, "Role of Rheology in Barite Sag in SBM and OBM," American Association of Drilling Engineers, 2004 Drilling Fluids Conference, Houston, Texas, Apr. 6-7, 2004.

\* cited by examiner

METHODS AND SYSTEMS FOR CHARACTERIZING LCM PARTICLE PLUGGING AND RHEOLOGY IN REAL TIME

BACKGROUND

The present invention relates generally to methods and systems for material characterization and more particularly, to methods and systems for characterizing drilling fluids laden with LCM (Lost Circulation Material) and other solid materials.

Drilling operations play an important role when developing oil, gas or water wells or when mining for minerals and the like. During the drilling operations a drill bit passes through various layers of earth strata as it descends to a desired depth. Drilling fluids are commonly employed during the drilling operations and perform several important functions including, but not limited to, removing the cuttings from the well to the surface, controlling formation pressures, sealing permeable formations, minimizing formation damage, and cooling and lubricating the drill bit.

When the drill bit passes through porous, fractured or vugular strata such as sand, gravel, shale, limestone and the like, the hydrostatic pressure caused by the vertical column of the drilling fluid exceeds the ability of the surrounding earth formation to support this pressure. Consequently, some drilling fluid is lost to the formation and fails to return to the surface. This loss may be any fraction up to a complete loss of the total circulating drilling fluid volume. This condition is generally known in the art as Lost Circulation. Failure to control Lost Circulation increases drilling cost and can damage formation production capabilities.

The general practice is to add any number of materials to the drilling fluid which act to reduce or prevent the outward flow of the drilling fluid in a porous and or fractured stratum thereby reducing or preventing Lost Circulation. The materials used in this process are commonly referred to as Lost Circulation Materials ("LCM"). Some materials typically used as LCM include, but are not limited to, wood fiber, popped popcorn, straw, bark chips, ground cork, mica, ground and sized minerals and the like.

In order to better understand the performance of a drilling fluid laden with LCM and/or other solid materials on the field, it would be desirable to characterize and study the drilling fluid. Currently, such tests are performed in the field. Field test are currently centered on the standard API configured HTHP filtration device. In this device the user can select porous media of various pore throat sizes. In some instances a flat plate with a slotted gap(s) has been used. However, performing such tests on the field has several disadvantages.

One disadvantage of the current approach is that the drilling fluid cannot be analyzed in detail since the analysis will be limited to the existing equipment such as the existing slot widths and angles. Moreover, performing such analysis in the field would be expensive and time consuming.

FIGURES

Some specific example embodiments of the disclosure may be understood by referring, in part, to the following description and the accompanying drawings.

Figure 1:
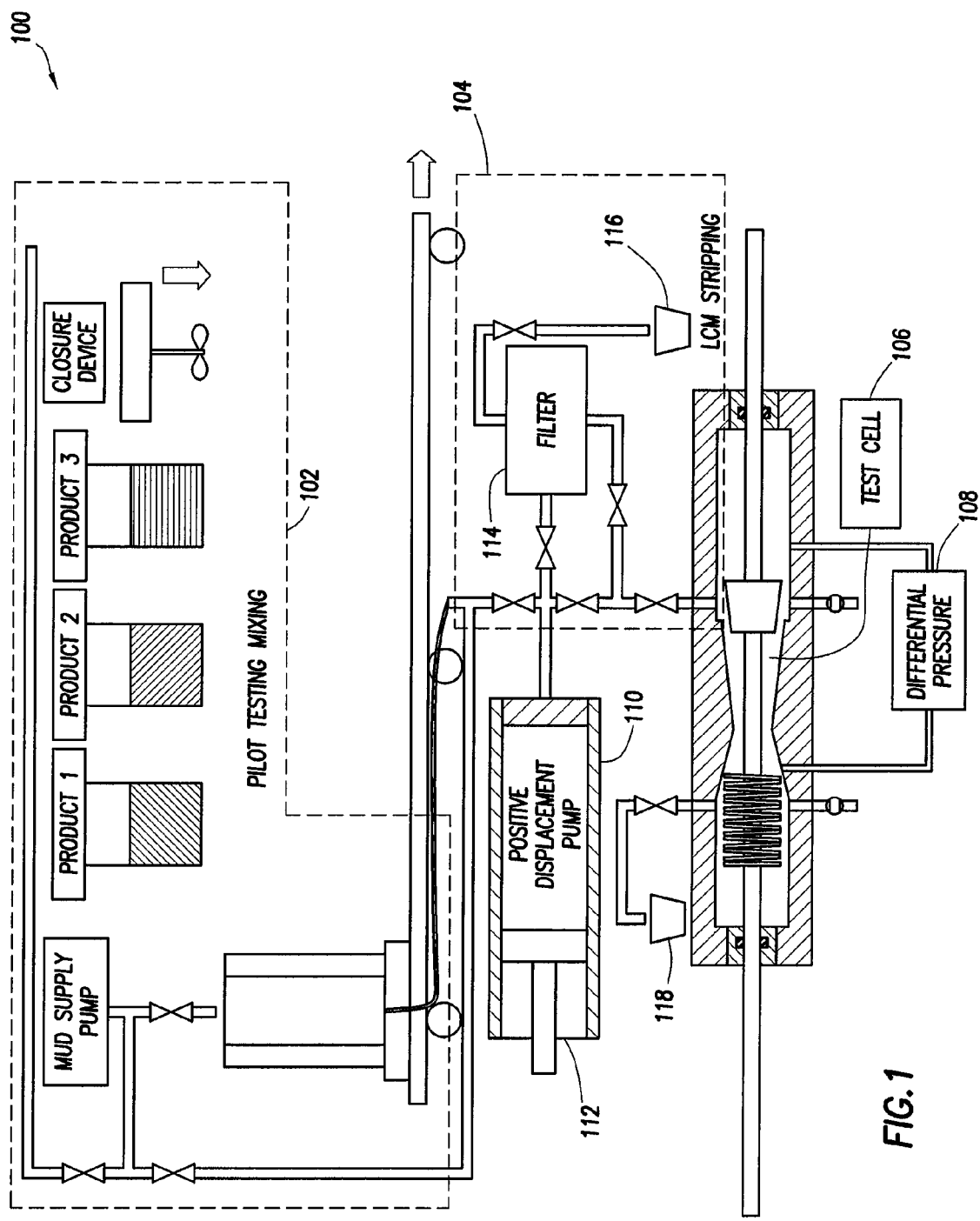
FIG. 1 is a characterization system in accordance with an exemplary embodiment of the present invention.

While embodiments of this disclosure have been depicted and described and are defined by reference to example embodiments of the disclosure, such references do not imply a limitation on the disclosure, and no such limitation is to be inferred. The subject matter disclosed is capable of considerable modification, alteration, and equivalents in form and function, as will occur to those skilled in the pertinent art and having the benefit of this disclosure. The depicted and described embodiments of this disclosure are examples only, and not exhaustive of the scope of the disclosure.

SUMMARY

The present invention relates generally to methods and systems for material characterization and more particularly, to methods and systems for characterizing drilling fluids laden with LCM (Lost Circulation Material) and other solid materials.

In one embodiment, the present invention is directed to a characterization system comprising: a pilot testing mixer system; a LCM stripping system coupled to the pilot mixer system; and a test cell coupled to the LCM stripping system.

In another exemplary embodiment, the present invention is directed to a test cell for analyzing a fluid comprising: a first conical inner portion; an axial positioning device positioned along an axis of the test cell; a first conical plug coupled to the axial positioning device; wherein the first conical plug is movable in and out of the first conical inner portion along the axis of the test cell; a fluid inlet at a first location on the test cell; and a fluid outlet at a second location on the test cell.

In another exemplary embodiment, the present invention is directed to a method of measuring the rheology of a first fluid comprising: passing the first fluid through a gap formed between a conical plug and a conical portion of a test cell; measuring a pressure drop along the gap; using the pressure drop measurement to determine a shear stress; measuring the flow rate of the first fluid through the gap; using the flow rate measurement and flow geometry to determine an average shear rate; and predicting rheological model parameters of the first fluid using the shear stress and the average shear rate.

In another exemplary embodiment, the present invention is directed to a method of optimizing sealing efficiency comprising: creating a gap between a conical plug and a conical portion in a test cell; wherein the gap width simulates a fracture width; flowing a first fluid through the gap; determining the sealing efficiency of the first fluid; clearing the gap; flowing a second fluid through the gap; determining the sealing efficiency of the second fluid; and determining which of the first fluid and the second fluid is more effective in sealing the gap. In one exemplary embodiment, the present invention is directed to a method of optimizing sealing efficiency comprising: creating a gap between a conical plug and a conical portion in a test cell; wherein the gap width simulates a fracture width; flowing a first fluid through the gap; determining the sealing efficiency of the first fluid; flowing a second fluid through the gap; determining the sealing efficiency of a mixture of the first fluid and the second fluid; and determining if the second fluid enhanced the sealing efficiency of the first fluid.

In another exemplary embodiment, the present invention is directed to a method of determining an optimal performance range for a fluid comprising: creating a gap between a conical plug and a conical portion in a test cell; flowing a fluid through the gap; determining the sealing efficiency of the fluid while changing the gap width; identifying a range of optimal performance gap widths for the drilling fluid.

The features and advantages of the present disclosure will be readily apparent to those skilled in the art upon a reading of the description of exemplary embodiments, which follows.

DESCRIPTION

The present invention relates generally to methods and systems for material characterization and more particularly, to methods and systems for characterizing drilling fluids laden with LCM (Lost Circulation Material) and other solid materials.

FIG. 1 depicts a characterization system 100 in accordance with an embodiment of the present invention. In one exemplary embodiment, the characterization system 100 comprises a Pilot Testing Mixer (PTM) system 102, a LCM Stripping system 104 coupled to the PTM system 102 and a test cell 106 coupled to the LCM Stripping system 104. As would be appreciated by those of ordinary skill in the art, two components are deemed coupled to each other when fluid can flow from one to the other. Moreover, coupling does not require that the components be directly connected.

Figure 2A:
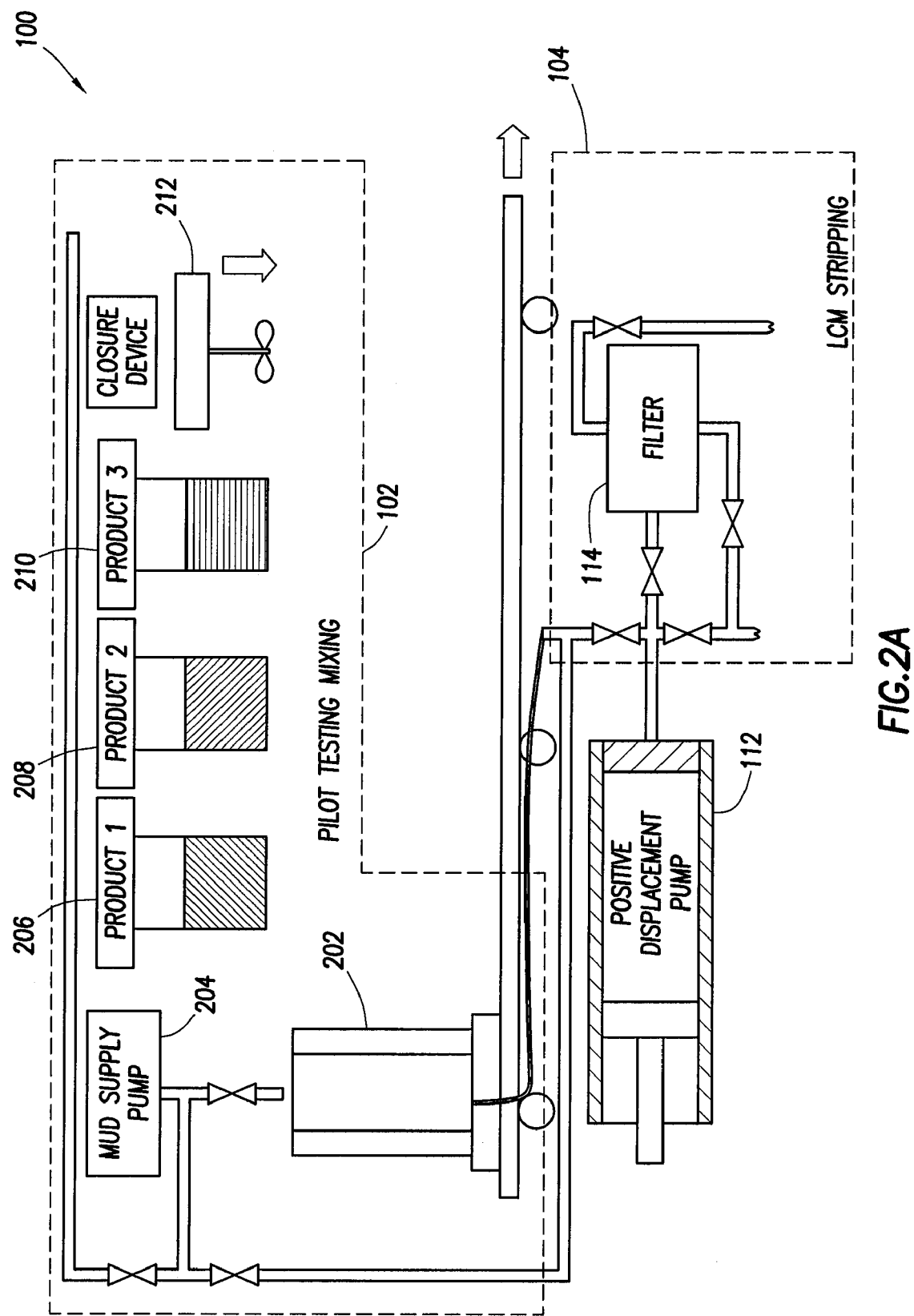
FIGS. 2A-2F depict the steps in preparing a sample drilling fluid.
Figure 2B:
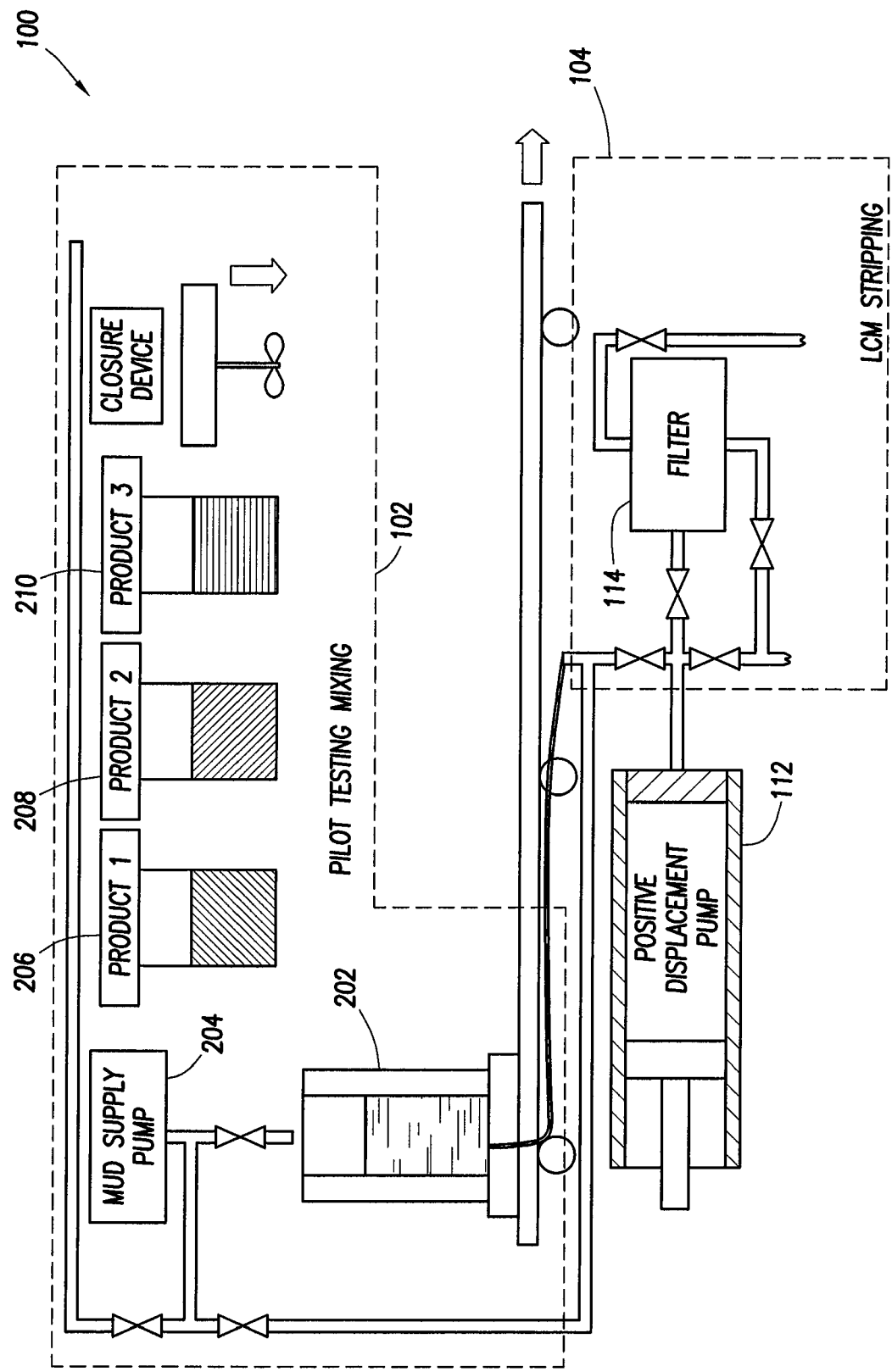
Figure 2C:
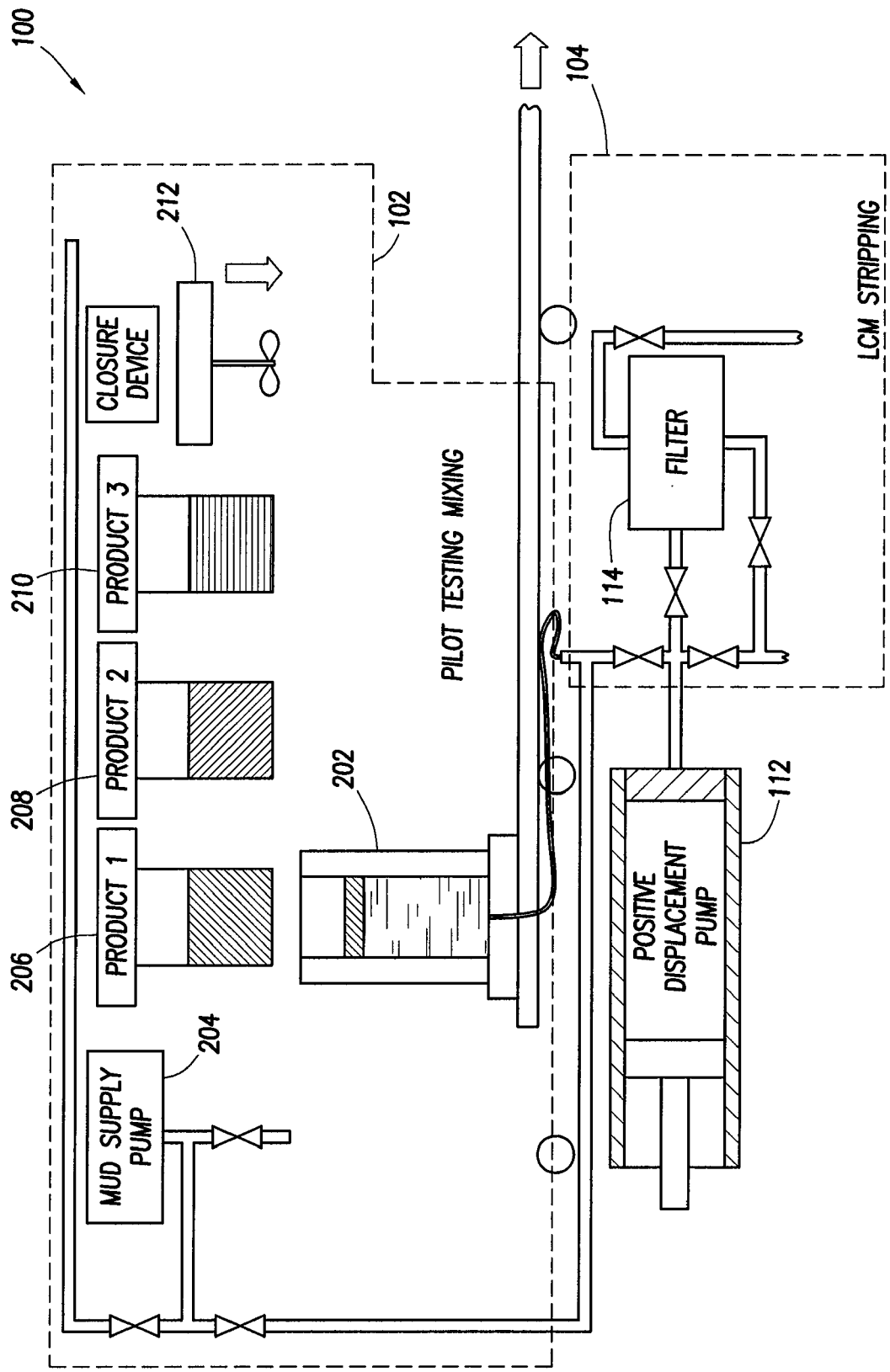
Figure 2D:
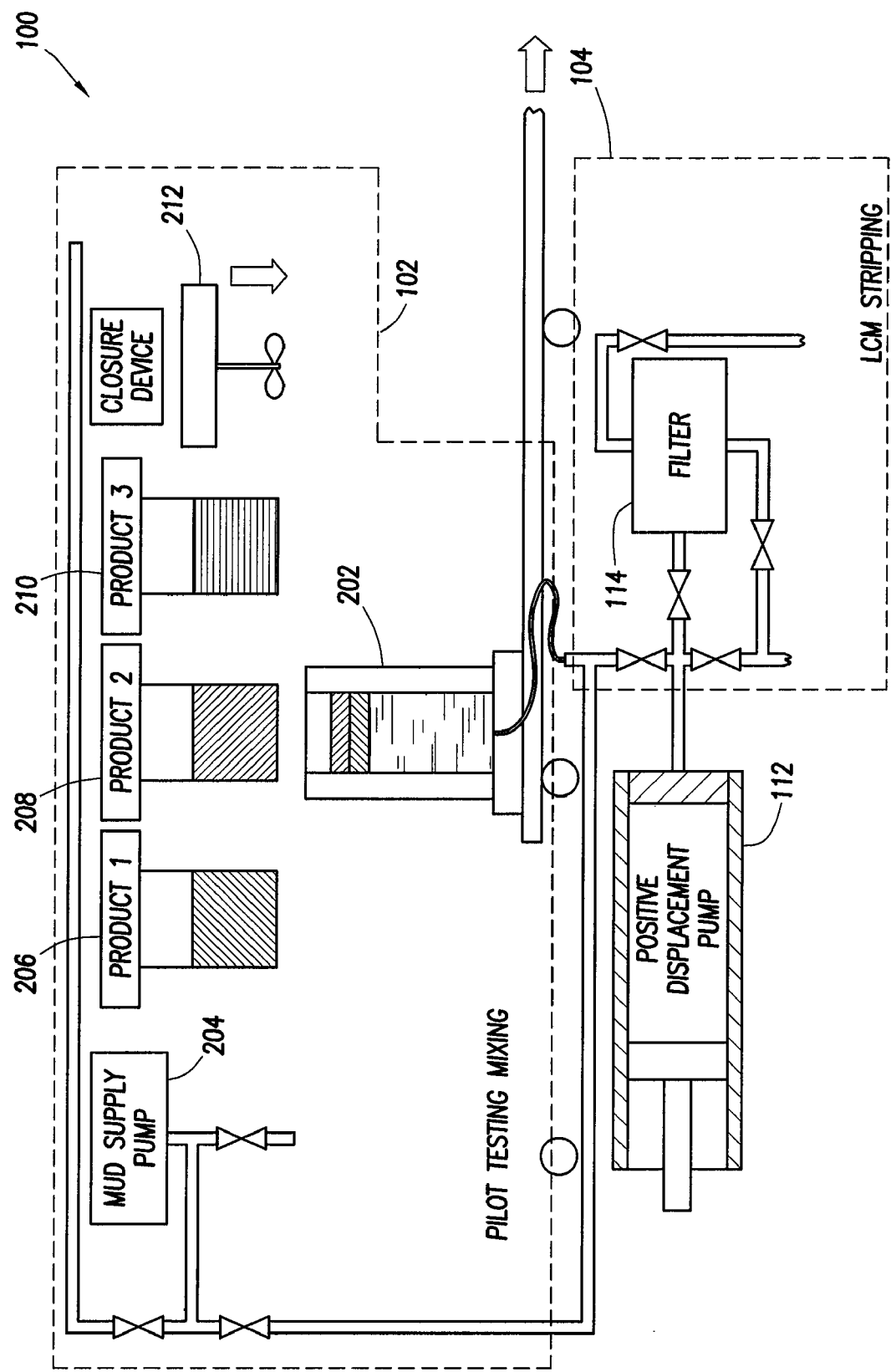
Figure 2E:
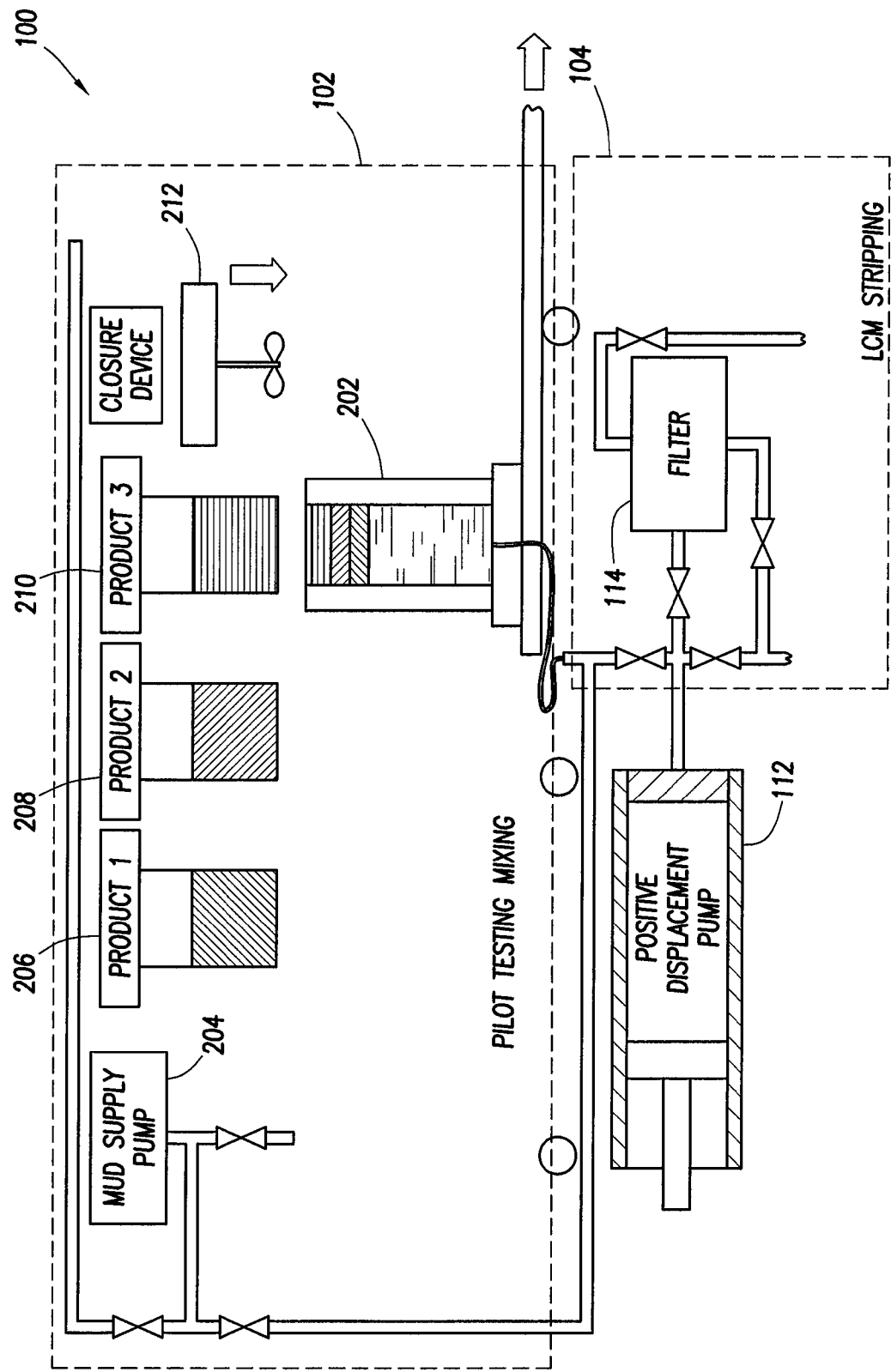
Figure 2F:
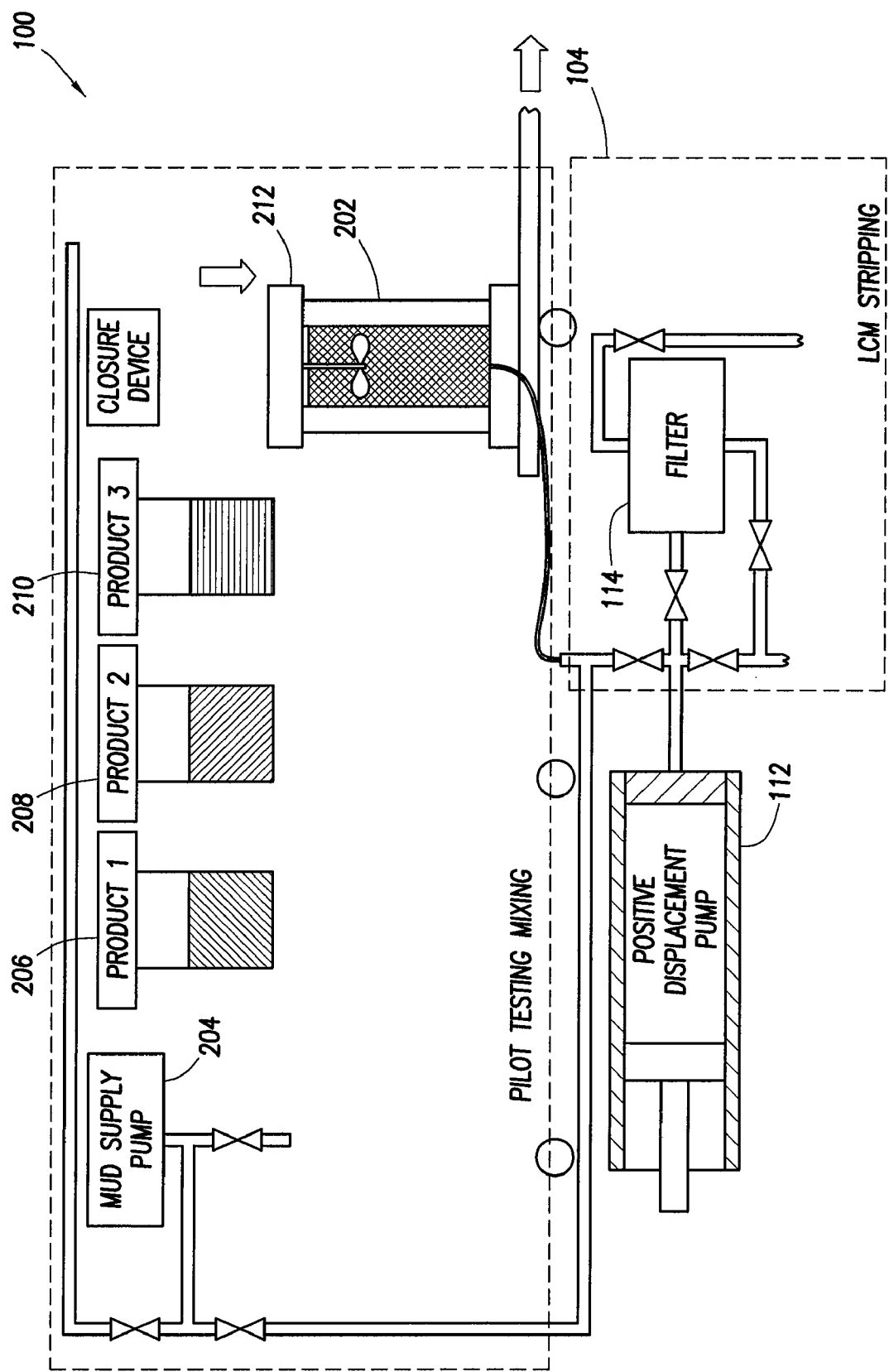

FIGS. 2A-2F depict the operation of the PTM system 102 where the drilling fluid to be analyzed is prepared. The PTM system 102 provides for addition and mixture of known quantities of LCM products to the drilling fluid. The PTM system 102 comprises a mixing tub 202 where the drilling fluid mixture is prepared. As depicted in FIG. 2A, a mud supply pump 204 first adds the drilling mud to the mixing tub 202. Once the drilling mud is added to the mixing tub 202 (FIG. 2B), the mixing tub 202 is placed in position for addition of different products from the product storage units 206, 208, 210. Product 1 (206), Product 2 (208) and Product 3 (210) are added to the mixing tub 202 as depicted in FIGS. 2C, 2D and 2E respectively. Although three products are depicted as being added to the mixing tub 202, as would be appreciated by those of ordinary skill in the art, with the benefit of this disclosure, one or more products may be added to the drilling mud depending on the drilling fluid being analyzed. Moreover, in one embodiment, there may be no products added to the drilling mud in order to analyze the drilling mud itself. Products 1, 2, and 3 may be LCM or other materials suitable for addition to the drilling mud.

Once all the products are added to the mixing tub 202, a closure device 212 closes the mixing tub 202 and mixes the contents therein preparing a desired drilling fluid mixture in the mixing tub 202. Each of the mud supply pump 204 and the product storage units (206, 208, 210) are in effect removably couplable to the mixing tub 202 and can be coupled to the mixing tub 202 for addition of materials and then be removed. Similarly, the closure device 212 is removably connectable to the mixing tub 202 and can be removed therefrom once it has performed the mixing operation. A pump 112 may then be used to deliver the drilling fluid mixture from the mixing tub 202 to the test cell 106. In one embodiment, a positive displacement pump may be utilized to deliver the drilling fluid mixture to the test cell 106.

Figure 3:
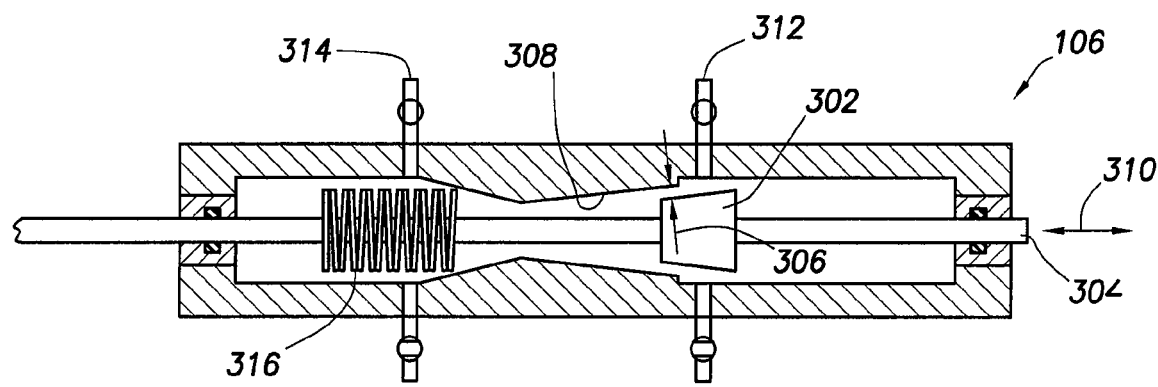
FIG. 3 is a test cell in accordance with an exemplary embodiment of the present invention.

FIG. 3 depicts an enlarged view of the test cell 106 which is where the measurements are actually made. The test cell 106 comprises a conical plug 302 coupled to an axial positioning device 304. The axial positioning device 304 may be used to axially position the conical plug 302 in a conical portion 306 formed by the test cell walls 308. The gap between the conical plug 302 and the test cell wall 308 simulates a fracture width. Different fracture widths may be simulated by moving the conical plug 302 in and out of the conical portion 306 in the direction indicated by the arrow 310. In addition to simulating the fracture width, the geometry of the test cell wall 308 can be specified so as to simulate a particular desired fracture angle. Consequently, the conical plug 302 and the test cell wall 308 can be utilized to simulate a range of fracture widths and angles providing the capability of analyzing the drilling fluid using a variable width slot. Stated otherwise, the slot width variability allows one to characterize the plugging and bridging of LCM products through a variety of user selectable fracture widths. The test cell also comprises a fluid inlet 312 and a fluid outlet 314. In one embodiment a brush 316 or other cleaning device may be coupled to the axial positioning device 304. The cleaning device may comprise one or more brushes or sponges. Alternatively, ultrasonic cleaning devices or jets may be used for cleaning the test cell walls 308. Another cleaning device could be positioned so that it cleans the plug 302. The brush 316 may be used to clean the test cell 106. After each test sequence the axial positioning device 304 may be used to move the brush 316 and perform a series of brush and rinse cycles to clean the test cell 106. As would be appreciated by those of ordinary skill in the art, with the benefit of this disclosure, a number of different materials may be used during the rinse cycle depending on the drilling fluid being tested. In one embodiment base oil or water may be used to rinse the test cell 106. The materials removed from the test cell 106 are transferred to a waste container 118.

Returning now to FIG. 1, in one embodiment the test fluid is pumped through the test cell 106 at a constant rate while measuring the differential pressure across the simulated fracture at 108. As would be appreciated by those of ordinary skill in the art, with the benefit of this disclosure, the differential pressure may be measured in a number of ways, including, but not limited to pressure transducers which may be used in pairs or differential pressure transducers. In another exemplary embodiment, the drilling fluid may be analyzed by setting the differential pressure and controlling the flow rate until plugging occurs. In one embodiment, a positive displacement pump 110 may be utilized to control the flow of the drilling fluid through the test cell 106. Although FIG. 1 depicts a positive displacement pump 110 configured as a syringe pump, as would be appreciated by those of ordinary skill in the art, with the benefit of this disclosure, any positive displacement pump capable of operating at the desired test pressure range may be used.

Figure 4:
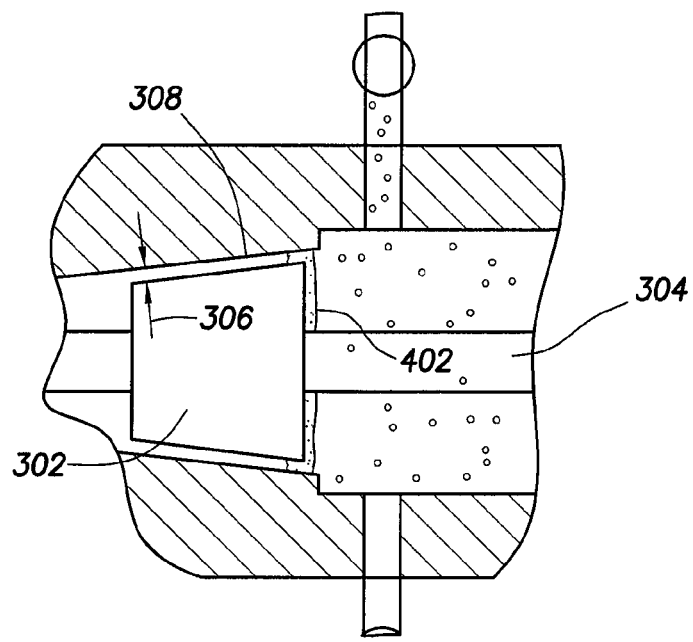
FIG. 4 is an enlarged view of a plug formed in a test cell in accordance with an exemplary embodiment of the present invention.

FIG. 4 depicts a simulated particle plugging and bridging in a test cell 106 in accordance with an embodiment of the present invention. As the drilling fluid is passed through the test cell 106 the LCM solids that bridge and plug 402 the simulated fracture in the conical portion 306 between the conical plug 302 and the test cell wall 308 may form a seal anywhere along the flow path. In the parallel slot mode, where the walls defining the slot are substantially parallel to one another, most plugging is likely to occur at or very near the entrance of the simulated fracture. In contrast, in the conical slot mode, where the walls defining the slot form a tapered slot, the plugging initiation location could be anywhere along the conical test cell wall 308, depending on Particle Size Distribution. As would be appreciated by those of ordinary skill in the art, with the benefit of this disclosure, in the tapered slot mode ultrasonic methods may be used to determine the bridging and sealing efficiencies along the simulated fracture path if desired.

Figure 5:
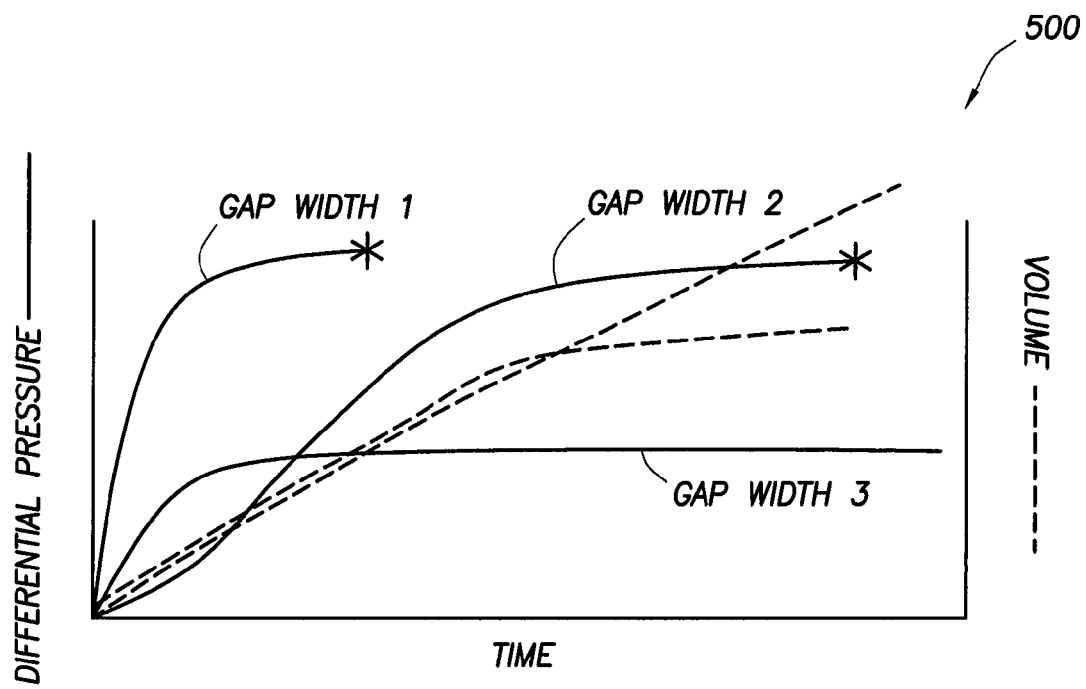
FIG. 5 depicts a graphical representation of the simulation of some expected test data from a test cell in accordance with an exemplary embodiment of the present invention.

FIG. 5 depicts a graphical representation of the simulation of some expected test data from the test cell 106. The graph 500 depicts three different gap width scenarios labeled Gap Width 1 through Gap Width 3 based on the change in differential pressure over time. The Gap Width 1 curve represents a scenario where the fracture plugs quickly and fluid flow through the fracture is completely shut off. The Gap Width 2 curve represents a scenario where the fracture plugs more slowly, but does eventually plug. Finally, in the curve labeled Gap Width 3 the flow continues and the fracture does not plug. The graph suggests that the fluid was treated sufficiently to plug the Gap Width 1. Because Gap Width 2 did plug but required more volume, the concentration of the ideal particle size was lower but yet at sufficient concentration to permit plugging. Therefore, the required particle availability could be established.

In one embodiment, the test cell 106 may be used to provide insitu and real time testing of various product mixtures to optimize sealing efficiency. As would be appreciated by those of ordinary skill in the art, with the benefit of this disclosure, a mixture has a high sealing efficiency if it can seal a fracture quickly and/or with the least amount of LCM materials. Stated otherwise, the simulated fracture structure of the test cell may be utilized as a pilot testing mechanism to minimize fluid loss and optimize LCM product usage. The methods and systems disclosed herein enable a determination of the sealing efficiency of a drilling fluid as a function of fracture width based on factors including, but not limited to, the rate of sealing and the total fluid loss for a fixed time period. The test cell 106 may first be used in the optimization mode thereby determining the best solution for a given fracture width. Specifically, the gap width in the test cell 106 may be configured to simulate a particular fracture width. A first drilling fluid is then passed through the gap and the efficiency of that drilling fluid in sealing the gap is determined. Next, after clearing the gap, a second drilling fluid is passed though the gap and its sealing efficiency is determined. The results are then compared to determine which of the first or the second drilling fluid performed more efficiently in plugging that gap. As would be appreciated by those of ordinary skill in the art, with the benefit of this disclosure, the sealing efficiency of a drilling fluid may be determined by determining the rate and ultimately the volume of the drilling fluid required to pass through the geometry before sealing occurs, with a smaller volume indicating a greater sealing efficiency. The same steps may be repeated in order to compare the sealing efficiency of a number of different drilling fluids for a particular gap width. The solution may then be tested at wider and narrower simulated fracture widths to determine a range of optimal performance for a particular solution, thereby minimizing performance uncertainty.

In an alternative embodiment, the gap is not cleared after the first drilling fluid is passed therethrough. Instead, after determining the sealing efficiency of the first drilling fluid, a second drilling fluid is passed through the gap. The sealing efficiency of the mixture of the first drilling fluid and the second drilling fluid is then measured to determine if the addition of the second drilling fluid has enhanced the sealing efficiency of the first drilling fluid.

In another exemplary embodiment, the test cell 106 may be used to measure the rheology of the drilling fluid. As would be appreciated by those of ordinary skill in the art, with the benefit of this disclosure, an invariant description of the flow properties of a Theologically complex fluid requires measurements in a steady or viscometric flow. There are three classes of such viscometric flow which include: (1) flow through a circular tube (Poiseuille), (2) flow through a thin slot or axially between concentric cylinders (Plane Poiseuille), and (3) flow between coaxially concentric rotating cylinders (Couette). In one embodiment, the present invention is directed to evaluating the rheology of an LCM fluid from measurements in the Plane Poiseuille class using formulae known to those of ordinary skill in the art, for computing nominal shear rate and shear stress from the flow rate and the pressure gradient.

Figure 6:
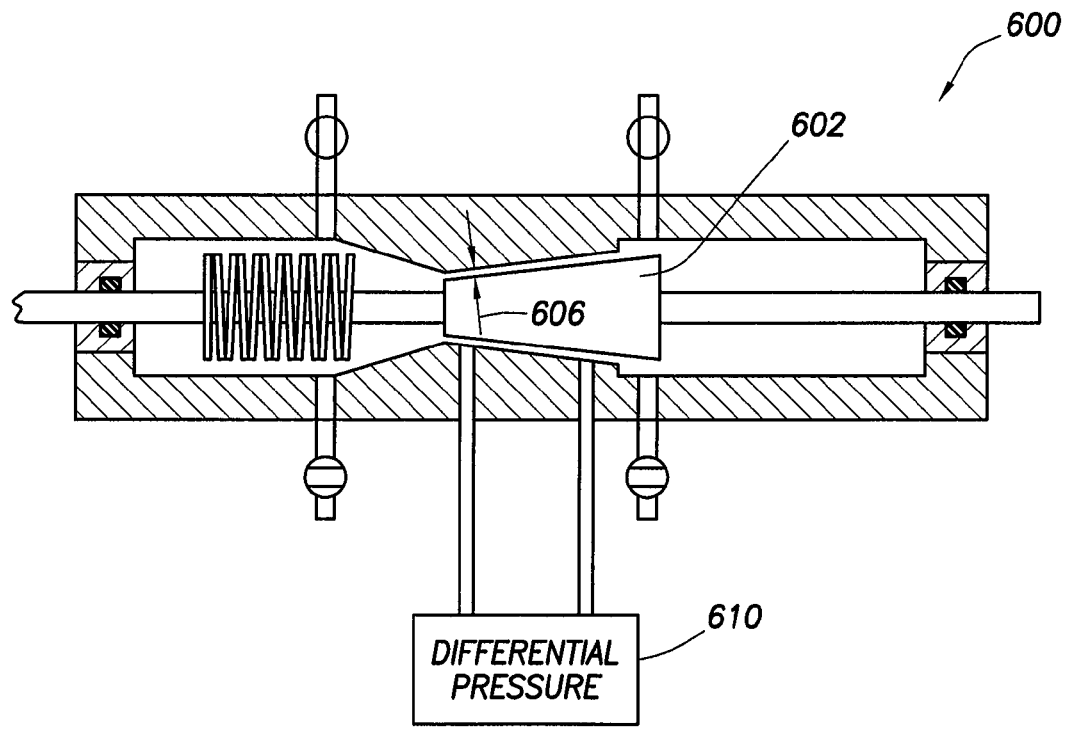
FIG. 6 depicts a test cell in accordance with an exemplary embodiment of the present invention.

In this mode of operation the configuration of the conical plug 302, the conical portion 306 and the variable slot width created provide the fundamental components of a rheometer. In this embodiment, the test cell 106 configuration may be modified as depicted in FIG. 6. The rheometer configuration test cell 600 may have a longer conical portion 606 and conical plug 602 and a different location for the differential pressure transducer 610 may be desirable as depicted in FIG. 6. The shear stress of the system may be determined by measuring the pressure drop along the conical portion 606 which simulates an annulus. Additionally, the flow rate would effectively provide an average shear rate. The resulting shear rate and shear stress values may be used to generate data to predict the Theological model parameters of the flow geometry like Plastic Viscosity (PV), Yield Point for the Bingham model (YP) and the different parameters of the Herschel-Bulkley model (n (power low exponent), k (consistency), and tau0 (yield stress). The shear rate in the conical portion 606 is not constant. However, as would be appreciated by those of ordinary skill in the art, with the benefit of this disclosure, it would be adequate to provide a simple method to provide basic mud engineering PV and YP, since the basic measurements for these numbers are at the higher shear rates and may be less sensitive to the geometry constraints. Moreover, as would be appreciated by those of ordinary skill in the art, with the benefit of this disclosure, the taper angle may be configured to approximate a constant shear rate.

In one embodiment the characterization system 100 may be used to obtain treated fluid rheology by comparing the pressure drops of a LCM laden fluid to the LCM stripped fluid. In typical operations the conventional rheometers cannot characterize the viscosity increase of a LCM treated fluid because of these rheometers intolerance to certain particle sizes. Thus, the pressure drop comparison, or ratio, may be used to calculate an effective viscosity increase due to the LCM loading based on the following mathematical assumption:

$$U^* \equiv U_f/U_0 \approx \delta_f/\delta_0 \approx dp_f/dp_0$$

where $U^*$ is a non-dimensional viscosity ratio; $U_f$ represents the viscosity of the treated fluid; $U_0$ represents the viscosity of the untreated fluid; $\delta_f$ represents the shear stress of the treated fluid; $\delta_0$ represents the shear stress for the untreated fluid; $dp_f$ represents the pressure drop of a treated fluid; and $dp_0$ represents the pressure drop of the untreated fluid as measured in the test cell. In one embodiment the ratio of the treated fluid pressure drop to the untreated fluid pressure drop may be used in conjunction with conventional shear rate, shear stress measurements of untreated fluid to approximate the treated fluid rheology. Untreated fluid rheology is typically measured by a FANN viscometer, available from Halliburton Energy Services of Duncan, Okla. In this analysis, the shear stress at each shear rate of the untreated fluid is simply multiplied by $U^*$ to obtain the treated fluid shear stress data at that shear rate.

These data then can then be processed into any suitable rheological model parameters and used in hydraulics equations. Consequently, the system disclosed herein would provide the real time Theological data for a treated fluid necessary to provide hydraulic calculations for LCM treated fluids that are all but impossible to measure in the field with conventional equipment.

Additionally, the test cell 106 disclosed herein provides the ability to measure the rheology of the LCM laden fluid relative to that of the LCM particle free fluid. The ability to characterize the treated fluid rheology would enable one to do hydraulic calculations prior to utilization of a treated fluid. This would ensure that the higher viscosity treated fluids will not cause the Equivalent Circulatory Density excursions beyond the fracture gradient during treatment applications or normal drilling.

In one exemplary embodiment the characterization system 100 of the present invention may be placed on a rig site permitting drilling fluid analysis prior to drilling through known trouble zones. Specifically, the characterization system 100 may systematically test a series of product additions prior to fluid exposure in a known problem zone. In one embodiment the test treatments may be selected in a number of ways, including, but not limited to using DFG Solids Modeling software available from Halliburton Energy Services of Duncan, Okla. Once tested and verified, the instrument will provide data to enable product and concentration recommendations, thereby providing high quality real time solutions to lost circulation problems. In another embodiment, the methods of the present invention may be employed during trouble mitigation. In this embodiment, when a problem zone is anticipated, various treatment scenarios may be tested to ensure appropriate treatment during the drilling process. As would be appreciated by those of ordinary skill in the art, with the benefit of this disclosure, some prior knowledge of what to expect typically comes from offset well data, In yet another exemplary embodiment the characterization system 100 may be used to verify whether the current LCM loading is adequate. In this mode of operation the test cell 106 would test the drilling fluid in an as received condition. Once the drilling fluid is tested by the test cell 106 it is passed through the LCM stripping system 104. The LCM material is then filtered out by the filter 114 and transferred to a waste container 116. The base mud exiting the filter may then be passed back to the test cell 106 to be analyzed. In this mode of operation the characterization system 100 may be utilized to quantify the plugging efficiency of the current LCM treatment as compared to the base mud. In another embodiment, once the base mud exits the filter 114 it is forwarded to the pilot testing mixing system 102. The pilot testing mixing system 102 may then introduce new LCM material(s) into the drilling mud which may be then passed back to the test cell 106 to compare the characteristics of different LCM treatments. As would be appreciated by those of ordinary skill in the art, with the benefit of this disclosure, the LCM stripping system 102 may be cleaned in a number of ways. In one embodiment, the LCM stripping system 102 may be cleaned by back flushing with a clean base fluid.

Figure 7:
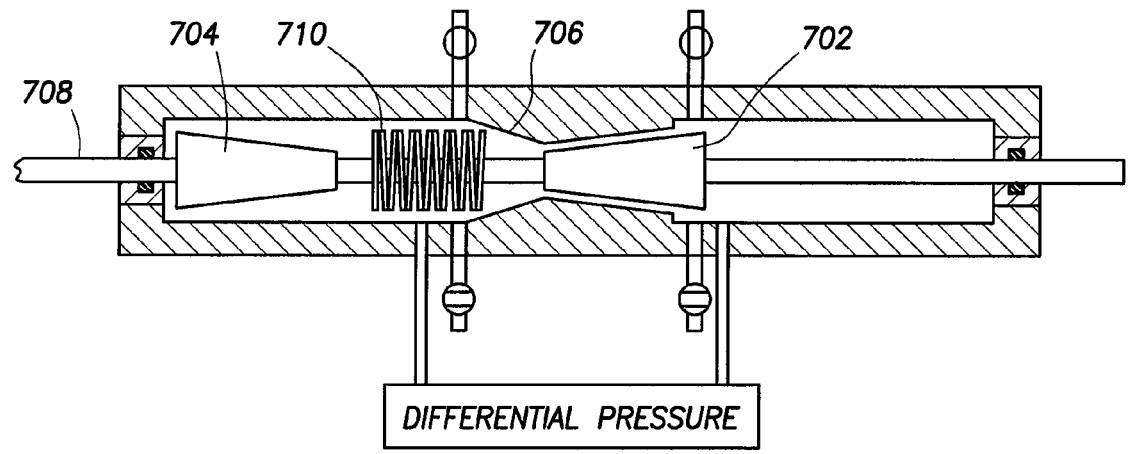
FIG. 7 depicts a test cell in accordance with an exemplary embodiment of the present invention.

Depicted in FIG. 7 is a test cell in accordance with another exemplary embodiment of the present invention. In this embodiment, the test cell comprises two conical plugs 702, 704 coupled to an axial positioning device 708. The first conical plug 702 and the second conical plug 704 may be at different tapered angles relative to the test cell wall 706. The axial positioning device 708 may be utilized to move the first conical plug 702 and the second conical plug 704 together or independently. A brush 710 may be used to clean the test cell as described above with respect to FIG. 3. This embodiment allows testing to be performed in either direction providing for investigation of different simulated fracture angles.

Figure 8:
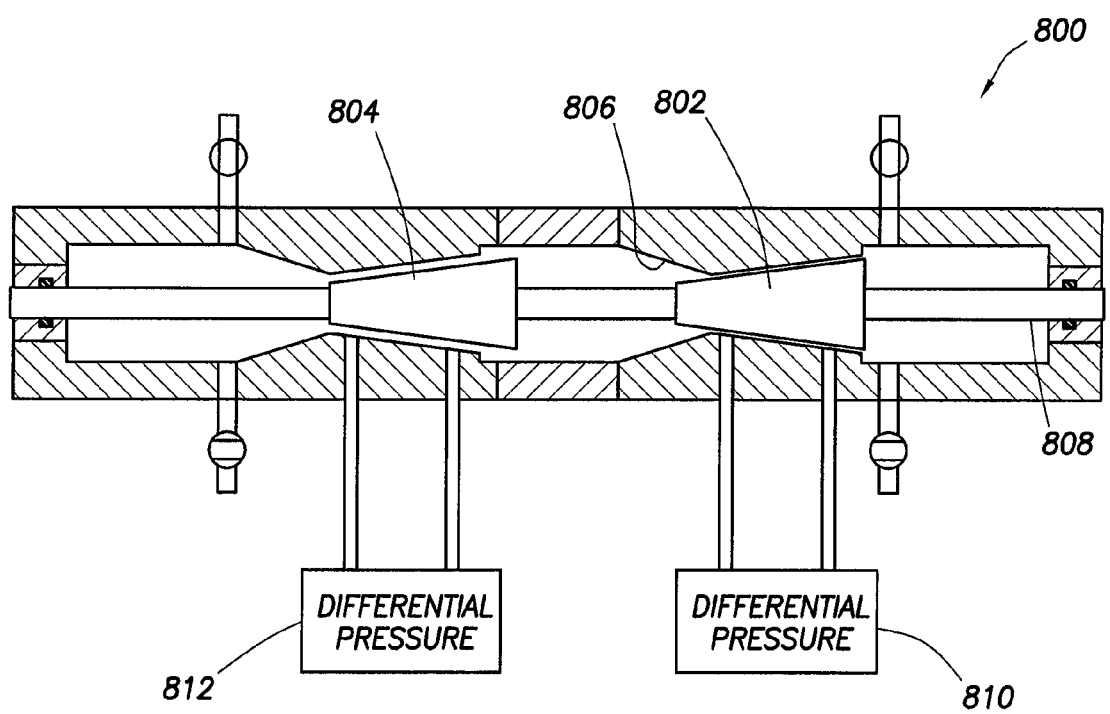
FIG. 8 depicts a test cell in accordance with an exemplary embodiment of the present invention.

FIG. 8 depicts a test cell in accordance with yet another exemplary embodiment of the present invention. A first conical plug 802 and a second conical plug 804 are coupled to an axial positioning device 808 and positioned so as to form different gap widths with the test cell wall 806. The axial positioning device 808 may be utilized to move the first conical plug 802 and the second conical plug 804 together or independently. As would be appreciated by those of ordinary skill in the art, with the benefit of this disclosure, the simplicity of this configuration allows for one pump rate to yield two shear rates. Consequently, rheology results may be obtained using a fixed geometry. A brush (not shown) may be used to clean the test cell 800 as described above with respect to FIG. 3. This arrangement provides for a simplified testing of rheology. In this embodiment, two different differential pressures 810, 812 may be measured at one pump rate and the pump rate may be fixed to approximate the required shear rate. In one exemplary embodiment the shear thinning effect may be determined by comparing the differential pressure ratios measured at various pump rates.

In another exemplary embodiment (not shown), a third conical plug may be added to the configuration illustrated in FIG. 8. The third conical plug provides a third gap width, so that with three different constant pump rates the operating range of the measurements is increased to nine different shear rates. The capability to manipulate the gap widths and the flow rates makes it possible to selectively evaluate rheological behavior in a low shear rate regime where viscoplastics exhibit their "yield stress" behavior and a broad class of shear thinning fluids exhibit "Newtonian-like" behavior. Additionally, as would be appreciated by those of ordinary skill in the art, with the benefit of this disclosure, rheological behavior may be evaluated in intermediate shear rate regime where details of the shear rate dependent viscosity function are revealed, and in the "upper Newtonian-like" regime. Moreover, as would be appreciated by those of ordinary skill in the art, with the benefit of this disclosure, a broad range of shear rates enhances the characterization of flow behavior and the probability of defining the rheological model that best describes the rheology of any fluid that will not plug the gaps.

This exemplary embodiment enhances the evaluation of the yield stress parameter which represents the minimum shear stress required to initiate a shearing flow and reflects the transition between solid-like (elastic, Hookean, etc.) behavior and viscous-like (Newtonian, shear thinning, etc.) behavior. This parameter is important in defining the flow behavior of a class of systems that exhibit viscoplastic behavior, such as certain formulations of drilling muds. As would be appreciated by those of ordinary skill in the art, with the benefit of this disclosure, an increase in yield stress is followed by increases in apparent viscosities and annular pressure losses. It is also well known that an increase in annular pressure loss is followed by an increase in the Equivalent Circulating Density ("ECD"). Hence the yield stress is particularly important in minimizing excursions or upsets in "ECD".

As would be appreciated by those of ordinary skill in the art, the ECD represents the effective hydraulic pressure exerted on the bottom of the wellbore by the combined effects of mud density and the total annular pressure loss resulting from hydraulic friction losses generated as the drilling fluid circulates through the annular channels in the drill string. As would be appreciated by those of ordinary skill in the art, with the benefit of this disclosure, it is desirable to maintain laminar flow in the annular channels of the drill string. Moreover, the annular friction losses are highly sensitive to the value of the yield stress, with a lower yield stress indicating a lower total annular pressure loss. Consequently, a lower yield stress will reduce the contribution of the annular pressure loss to the ECD value. Moreover, as would be appreciated by those of ordinary skill in the art, with the benefit of this disclosure, although the present invention is described as using a conical plug, it is possible to use a plug having a different shape in another embodiment without departing from the scope of the present invention. For instance, the plug may comprise a series of wedge shaped plugs and corresponding test cell walls.

Although the present invention is discussed herein in the context of drilling fluids, as would be appreciated by those of ordinary skill in the art, with the benefit of this disclosure, the methods and systems of the present invention may be utilized in analyzing other fluids. Moreover, as would be understood by those of ordinary skill in the art, with the benefit of this disclosure, the characterization system 100 may perform in one or any combination of the modes of operation discussed above. For instance, in one exemplary embodiment the test cell 106 may be utilized in a combined mode of operation thereby providing rheology measurement of the treated fluid as well as fluid optimization.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present invention. In addition, the terms in the claims have their plain, ordinary meaning unless otherwise explicitly and clearly defined by the patentee.

What is claimed is:

1. A test cell for analyzing a fluid comprising:
    a first conical inner portion;
    an axial positioning device positioned along an axis of the test cell;
    a first conical plug coupled to the axial positioning device;
    wherein the first conical plug is movable in and out of the first conical inner portion along the axis of the test cell;
    wherein the axial positioning device moves the first conical plug along the axis of the test cell;
    a fluid inlet at a first location on the test cell;
    a fluid outlet at a second location on the test cell; and
    a brush coupled to the axial positioning device.

2. The test cell of claim 1, further comprising a positive displacement pump, wherein the positive displacement pump controls fluid flow through the test cell.

3. The test cell of claim 1, further comprising:
    a second conical plug coupled to the axial positioning device;
    wherein the second conical plug is movable in and out of a second conical inner portion along the axis of the test cell.

4. The test cell of claim 3, further comprising:
    a third conical plug coupled to the axial positioning device;
    wherein the third conical plug is movable in and out of a third conical inner portion along the axis of the test cell.

5. The test cell of claim 4, wherein each of the first conical plug, the second conical plug and the third conical plug is independently movable by the axial positioning device.

6. The test cell of claim 1, wherein the test cell at least one of measures a rheology of the fluid, optimizes sealing efficiency of the fluid, and determines an optimal performance range for the fluid.

* * * * *